(12) United States Patent
Wang

(10) Patent No.: US 7,913,428 B2
(45) Date of Patent: Mar. 29, 2011

(54) ELECTROMAGNETIC FITNESS SHOES WITH A CONDUCTOR STRUCTURE

(76) Inventor: Ching-Hung Wang, Taichung (TW)

( * ) Notice: Subject to any disclaimer, the term of this patent is extended or adjusted under 35 U.S.C. 154(b) by 852 days.

(21) Appl. No.: 11/780,800

(22) Filed: Jul. 20, 2007

(65) Prior Publication Data

US 2009/0019725 A1    Jan. 22, 2009

(51) Int. Cl.
*A43B 5/00*    (2006.01)
*A43B 13/38*    (2006.01)

(52) U.S. Cl. .................................. 36/132; 36/1; 36/44

(58) Field of Classification Search .................. 36/132, 36/144, 43, 136; 361/224, 223
See application file for complete search history.

(56) References Cited

U.S. PATENT DOCUMENTS

| | | | | |
|---|---|---|---|---|
| 2,279,094 A | * | 4/1942 | Siers | 361/224 |
| 2,407,189 A | * | 9/1946 | Taber, Jr. et al. | 361/224 |
| 3,007,083 A | * | 10/1961 | MacQuaid, Jr. et al. | 361/224 |
| 3,079,530 A | * | 2/1963 | MacQuaid et al. | 361/224 |
| 3,541,389 A | * | 11/1970 | Van Name | 361/224 |
| 3,641,688 A | * | 2/1972 | von den Benken | 36/43 |
| 5,319,867 A | * | 6/1994 | Weber | 36/44 |
| 5,994,245 A | * | 11/1999 | Marier et al. | 442/373 |
| 6,219,942 B1 | * | 4/2001 | Fini | 36/93 |
| 6,549,391 B1 | * | 4/2003 | Bisson | 361/223 |
| 7,471,497 B1 | * | 12/2008 | Knight et al. | 361/224 |

* cited by examiner

*Primary Examiner* — Ted Kavanaugh
(74) *Attorney, Agent, or Firm* — Egbert Law Offices PLLC

(57) ABSTRACT

The present invention provides electromagnetic fitness shoes with a conductor structure and an insole. The shoes include a vamp, an inner space, a heel portion and a sole. The sole includes a big sole body, a middle sole and an insole. The insole is provided with conducting members, and the conductor structure electrically connects to a conducting member. The conducting member includes a conductive terminal and electric wire. The conductive terminal fitted with an electric connecting portion. The conductive terminal is assembled into the interleaving space formed by the heel portion and arranged along the interleaving space. The electric connecting portion is exposed upwards, and the conducting member of insole is made of conductive fabrics. The robustness is improved, and the service life of the electromagnetic fitness shoes is prolonged with better comfort and applicability.

5 Claims, 6 Drawing Sheets

ELECTROMAGNETIC FITNESS SHOES WITH A CONDUCTOR STRUCTURE

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates generally to electromagnetic fitness shoes, and more particularly to innovative shoes with a conductor structure and insoles.

2. Description of Related Art Including Information Disclosed under 37 CFR 1.97 and 37 CFR 1.98

So-called electromagnetic fitness shoes refer to special shoes that combine positive and negative conducting members to generate physiotherapy and fitness effect for the benefit of human feet through medium to low cycle-by-cycle current. These shoes are perfectly suitable for modem people due to lack of space-time limitations.

As an innovative product marketed recently, some design issues for electromagnetic fitness shoes can only be observed during actual applications. The present invention intends to improve the conductor structure of electromagnetic fitness shoes, as typically disclosed by example in Taiwan patent No. M263007, entitled "Electromagnetic fitness shoes", wherein the conductive terminal is placed transversely on the heel wall of the shoes, and by another example in Taiwan patent No. M268955, entitled "Wire-controlled fitness shoes", wherein the conductive terminal is placed transversely on one side of the shoes.

However, there are the following shortcomings for these two typical structures observed during application. First, the electromagnetic fitness shoes are mainly used for walking purposes when they are not electrically activated, similar to sports shoes, leisure shoes, leather shoes or sandals. It is understood from everyday experience that shoes generally contact surrounding objects with friction and collision, so that the typical electromagnetic fitness shoes disclosed in Taiwan patent No. M263007 are extremely vulnerable to friction and collision in normal walking purposes, leading to damage and malfunction. Second, as for structural strength, the vertical wall of the heel is very thin, so a transverse portion of the conductive terminal is hard to be positioned firmly and robustly. As disclosed in Taiwan patent No. M268955, the heel is located nearer to the ground, so the conductive terminal is easily exposed to dampness and dust, bringing about an adverse effect on the functions of the shoes and a shorter service life.

In addition, the insoles of electromagnetic fitness shoes generally contact the feet to yield the electrical contact effect. Thus, metallic conducting strips with positive and negative electrodes are typically placed on the insole surface to electrically contact the human feet. However, it is observed from application that users may feel uncomfortable when stepping on the insoles, since the metallic conducting strips are rigid and solid and distributed in several patterns depending upon the design requirements. Therefore, such insoles are not well-suited for either electric treatment or general walking.

Thus, to overcome the aforementioned problems of the prior art, it would be an advancement in the art to provide an improved structure that can significantly improve efficacy.

Therefore, the inventor has provided the present invention of practicability after deliberate design and evaluation based on years of experience in the production, development and design of related products.

BRIEF SUMMARY OF THE INVENTION

The conductive terminal is arranged along an interleaving space formed between inner and external walls of the heel portion, so that the conductive terminal can be supported firmly without the protruding pattern of a typical prior art structure. Collisions are avoided and the robustness of the conductor structure are more robust for a longer service life.

Since the electric connecting portion of the conductive terminal is exposed at a top of the heel portion, a higher location on the shoe body, it is now feasible to greatly reduce the possibility of moisture and dust deposits on the conductive terminal. The normal functions are maintained, and the service life is effectively prolonged.

Based upon the conductive terminal arranged along the interleaving space of the heel portion, the conductive terminal is positioned firmly through overlapping or interleaving of inner and external walls of the heel portion, providing a more cost-efficient manufacturing process with better industrial efficiency.

Based on the linear characteristics of the end of electric wire, the overlapping length of electric wire and conducting member are extended, improving the stability of electric connections and eliminating the adverse influence from the offset of insole.

Based on the conducting member being made of conductive fabrics, the shoes provide better comfort and applicability.

In addition, a gasket is embedded into the through-hole penetrating the stepping surface and bottom of the insole, so that conductive fabric can be positioned firmly without being influenced by the offset. The gasket is made of elastic materials to improve walking comfort.

Although the invention has been explained in relation to its preferred embodiment, it is to be understood that many other possible modifications and variations can be made without departing from the spirit and scope of the invention as hereinafter claimed.

DETAILED DESCRIPTION OF THE INVENTION

Figure 1:
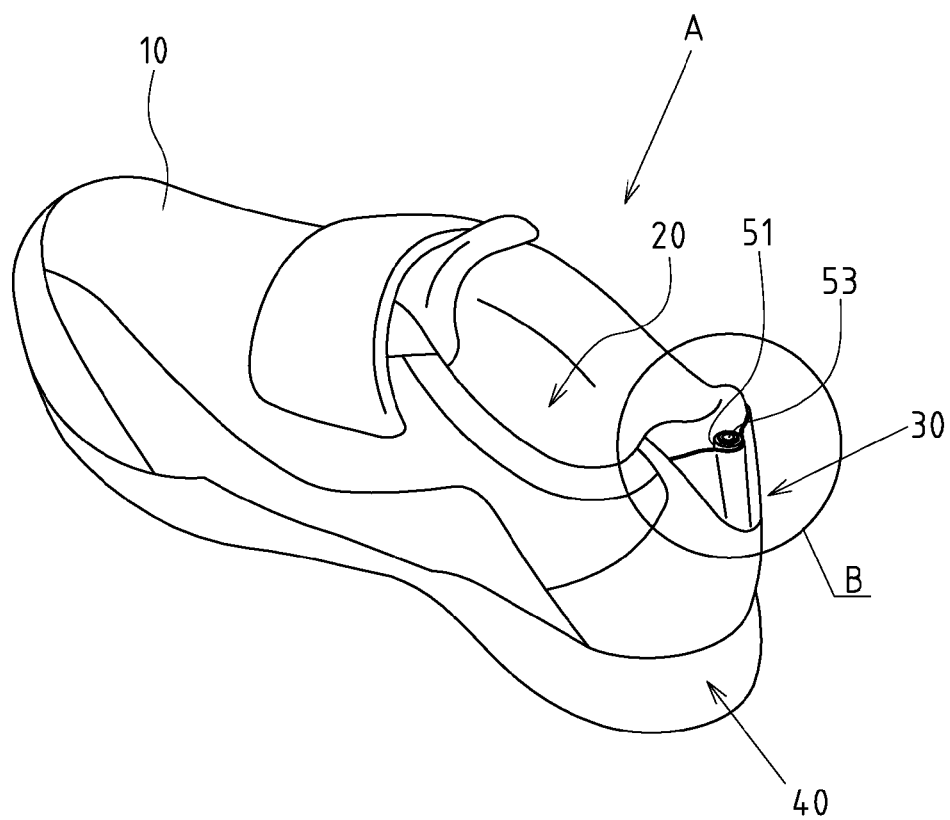
FIG. 1 shows an exploded perspective view of electromagnetic fitness shoes of the present invention.
Figure 2:
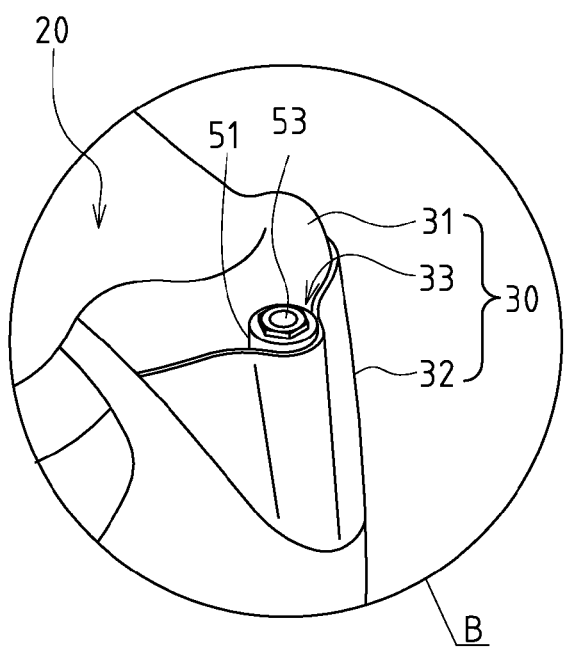
FIG. 2 shows a partially enlarged perspective view of position B of FIG. 1.
Figure 3:
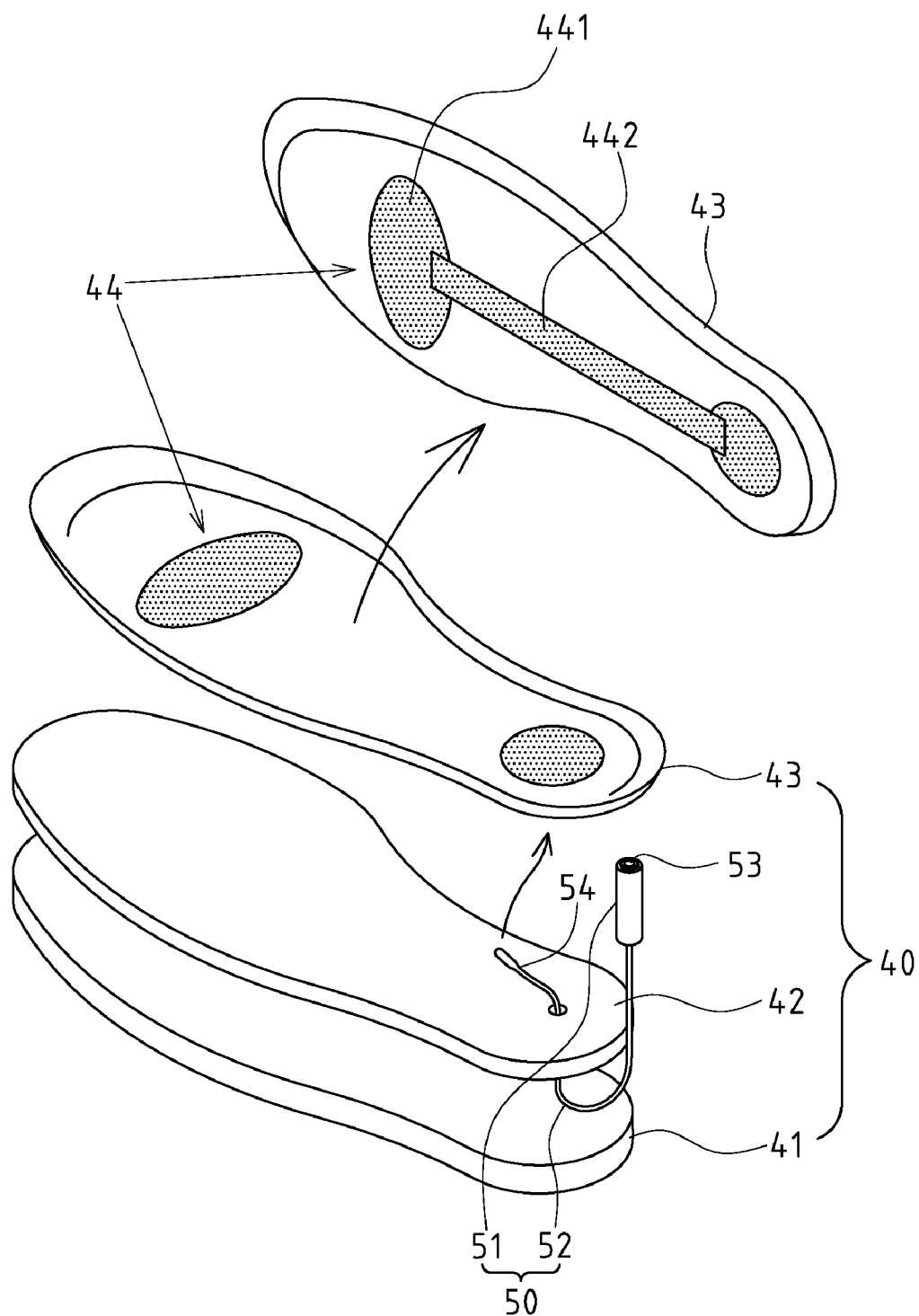
FIG. 3 shows an exploded perspective view of partial component of the present invention.
Figure 4:
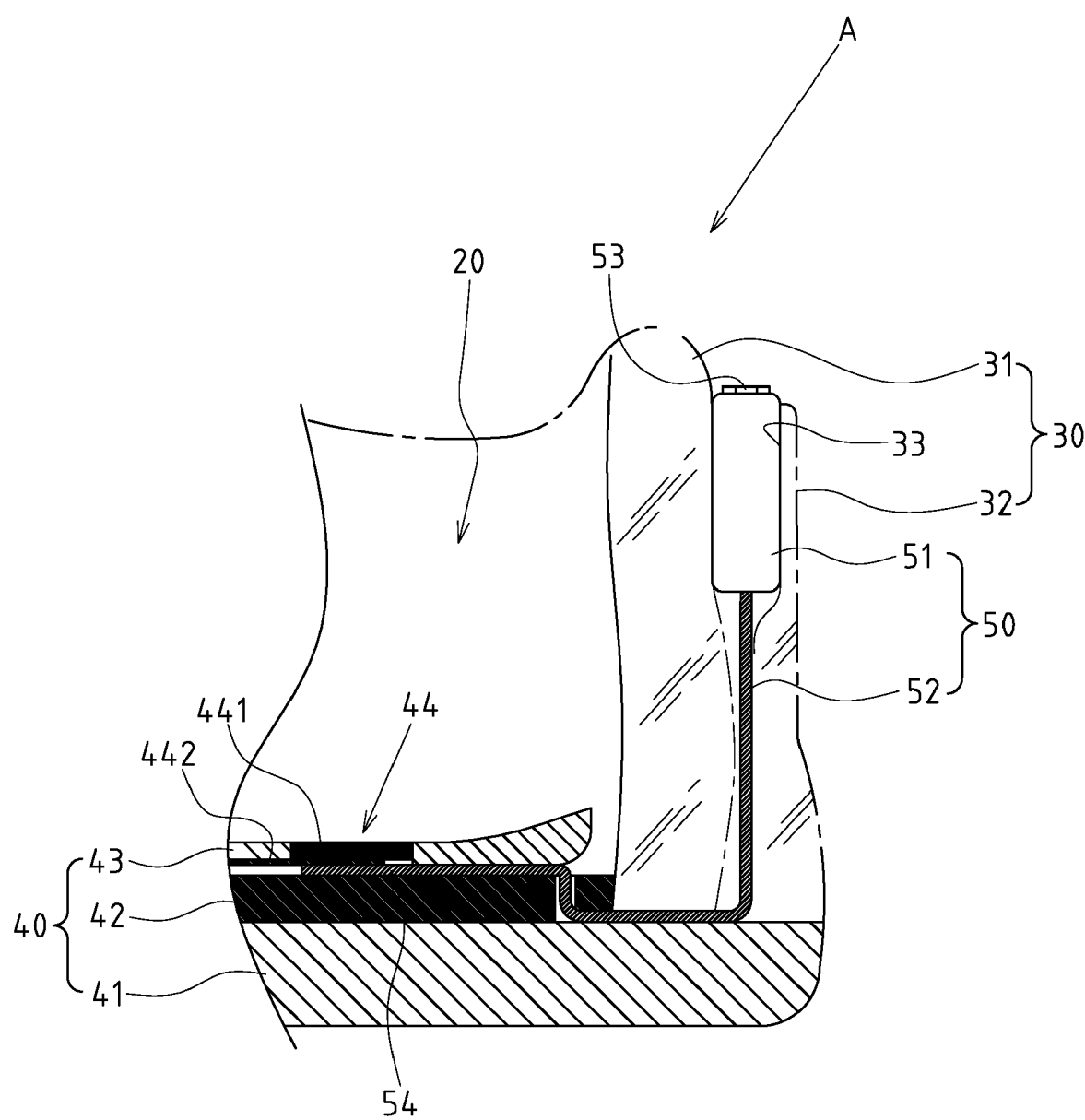
FIG. 4 shows an assembled sectional view of internal structure of the present invention.

The features and the advantages of the present invention will be more readily understood upon a thoughtful deliberation of the following detailed description of a preferred embodiment of the present invention with reference to the accompanying drawings.

FIGS. 1-4 depict preferred embodiments of the electromagnetic fitness shoes with a conductor structure and insoles of the present invention. The embodiments are provided only for explanatory purposes.

The electromagnetic fitness shoes comprises a shoe body A, which includes a vamp 10, an inner space 20, a heel portion 30 and a sole 40. The sole 40 comprises a big sole 41, a middle sole 42 and an insole 43. The insole 43 is fitted with conducting member 44. The conductor structure 50 connects electrically with the conducting member 44 of the insole 43 and comprises a conductive terminal 51 and an electric wire 52. One end of the conductive terminal 51 is provided with an electric connecting portion 53 (either a jack or a button pattern) for electrically linking one end of the preset electric wire. The other end of the electric wire is generally linked to a controller, thereby regulating the degree of electric wave generated from input current.

A major feature of the present invention is the conductive terminal 51 being assembled into an interleaving space 33 formed between inner wall 31 and external wall 32 of the heel portion 30 and being arranged along the interleaving space. One embodiment shows the conductive terminal 51 vertically arranged. Meanwhile, the electric connecting portion 53 of the conductive terminal 51 is exposed upwards. The electric wire 52 is transversely penetrated from the bottom of heel portion 30 into the bottom of middle sole 42 and then extended from the preset position of middle sole 42 to the top of middle sole 42. Moreover, the end 54 of the electric wire 52 is allowed for extending to the corresponding position of conducting member 44 of the insole 43 for electric connection.

The end 54 of the electric wire 52 may be designed into a linear shape. The electric wire 52 is overlapped with the conducting member 44, thereby improving the stability of electric connection and eliminating the adverse influence from the offset of insole 43.

Based upon above-specified structures of the electromagnetic fitness shoes of the present invention, when the users are intended for electrical activation, the preset end of electric wire inserts into electric connecting portion 53 of the conductive terminal 51. When the electric wire is energized, the current may be guided from the conductive terminal 51 to the end 54 via the electric wire 52, and then to the conducting member 44 of insole 43, thus enabling physiotherapy for the reflecting regions of the human feet. With regard to the arrangement of said conducting member 44, the positive and negative electrodes may be arranged onto the insoles 43 of either left or right foot, or collectively on the insoles 43 of a single foot.

Figure 5:
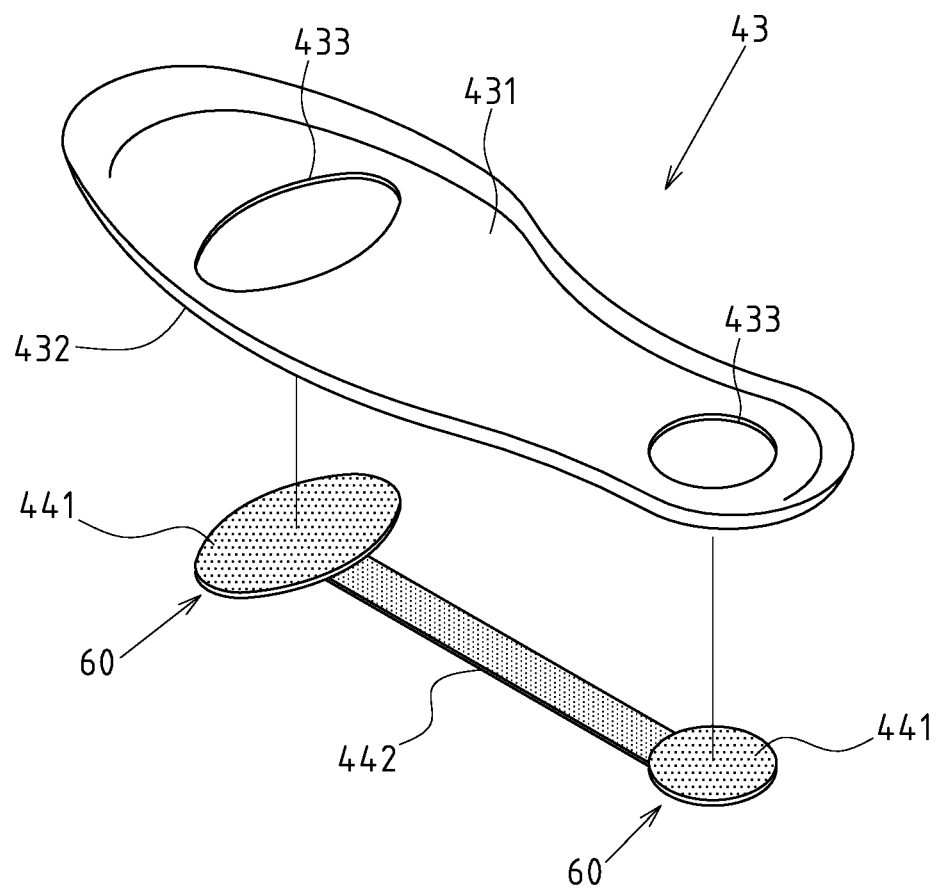
FIG. 5 shows an exploded perspective view of the preferred embodiment of insole structure of the present invention.
Figure 6:
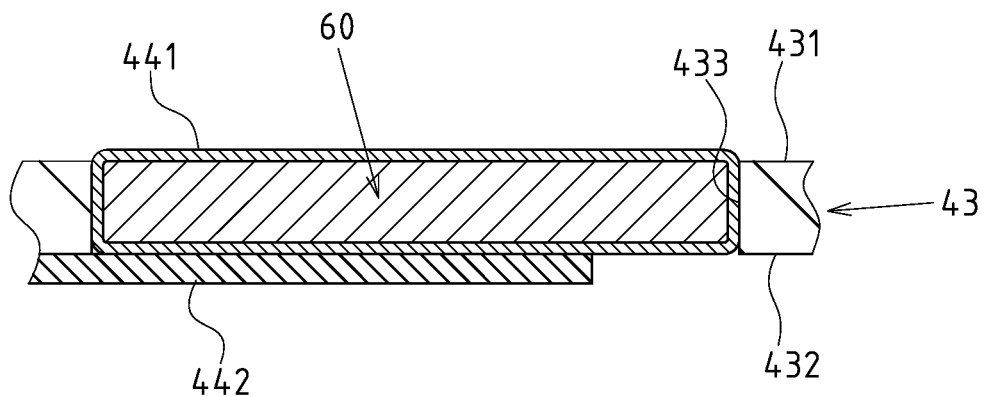
FIG. 6 shows a partially assembled sectional view of the preferred embodiment of insole structure of the present invention.

Referring to FIG. 5, the insole 43 is a plate with predefined thickness, from which a stepping surface 431 and a bottom 432 are defined. The conducting member 44 of the insole 43 is made of conductive fabric 441. A through-hole 433 penetrates the stepping surface and bottom on at least one region of the insole 10. Gaskets 60 (with the quantity in line with said through-holes 433) are additionally provided, which may be made of elastic materials (e.g. rubber and foaming materials). The gasket 60 is sized properly to be embedded into the through-hole 433 of the insole 43, so that conductive fabric 20 can adhere tightly onto the gasket 60, achieving electric connection of top and bottom conductive fabric 441 of the gasket 60. When the gaskets 60 arranged at interval are preset with the same electrode (i.e. positive or negative electrode), these two gaskets 60 can be linked by a conductive fabric 442 (shown in FIG. 5).

Figure 7:
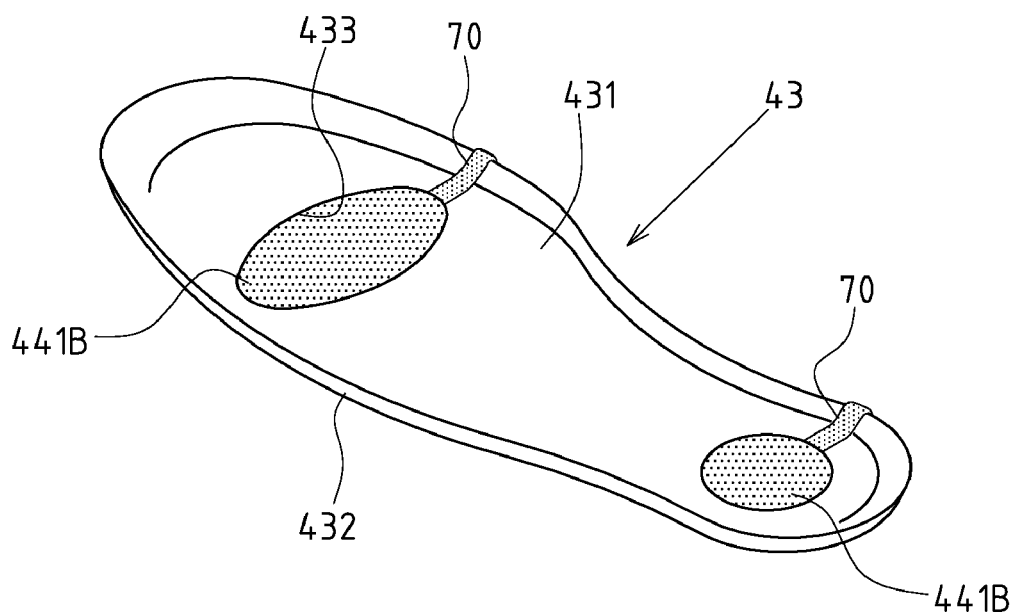
FIG. 7 shows a perspective view of another application of insole structure of the present invention.
Figure 8:
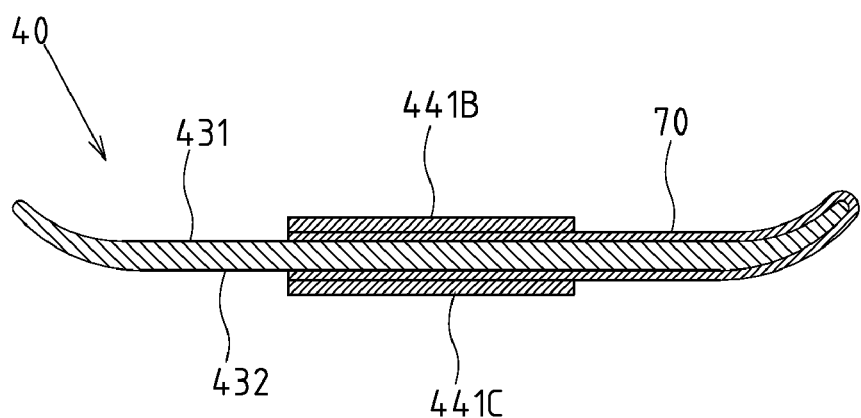
FIG. 8 shows a sectional view of another application of insole structure of the present invention.

FIGS. 7-8 depict another preferred embodiment of said conducting member, wherein the conductive fabrics 44 1B, 441C adhere separately onto the stepping surface 11 and bottom 12 of the insole 10 and are linked by a conductive body 70, thus providing electric connection of stepping surface 11, bottom 12 and corresponding conductive fabrics 441B, 441C. The conductive body 70 for linking stepping surface 11, bottom 12 and conductive fabrics 441B, 441C may also be made of conductive fabric. Moreover, the conductive body 70 can link conductive fabrics 441B, 441C from either side of the insole 10.

Figure 9:
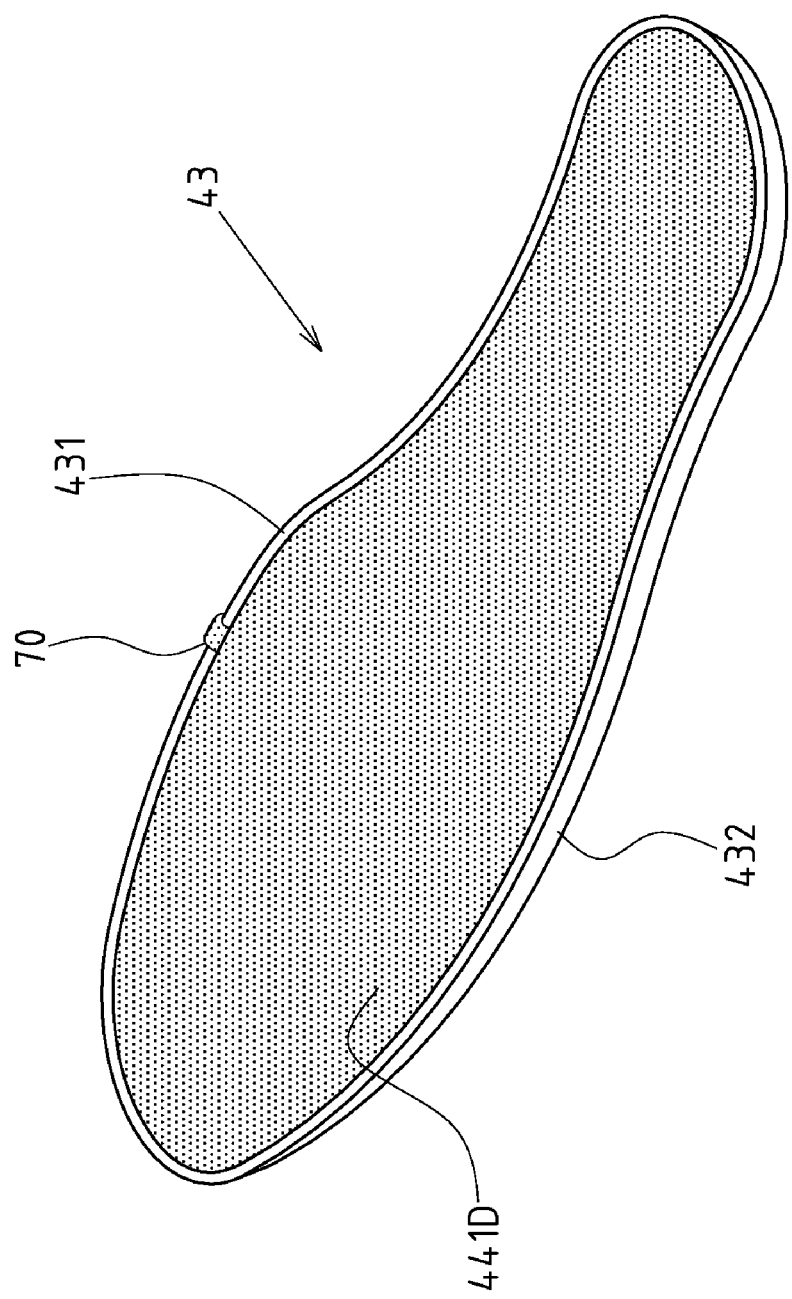
FIG. 9 shows a perspective view of another application of insole structure of the present invention.

Referring also to FIG. 9, the conductive fabric 441D is made of a large-sized block.

I claim:

1. A shoe assembly for supplying an electrical current to portions of a human foot, the shoe assembly comprising:
    a shoe body having a vamp and an inner portion and a heel portion and a sole, said sole having a bottom sole and a middle sole and an insole, said insole positioned at a bottom of said inner space so as to directly contact the human foot, said insole being a plate with a predetermined thickness, said insole defining a stepping surface and a bottom, said heel portion having an interleaving space formed between an inner wall and an external wall, said interleaving space being open at a top thereof, said sole being of a non-conductive material;
    a conducting member formed of a conductive fabric, said conducting member positioned on said insole so as to being a position suitable for passing electrical current to the human foot; and
    a conductor structure electrically connected to said conducting member, said conductor structure having a conductive terminal and an electric wire, one end of said conductive terminal having an electrical connecting portion , said conductive terminal positioned into said interleaving space so as to have said electric connecting portion exposed at the opening at said top of said interleaving space, said electric wire electrically connected to said conducting member.

2. The shoe assembly of claim 1, said electric wire transversely penetrating from said heel portion through said inner wall of said heel portion .

3. The shoe assembly of claim 2, said electric wire extending vertically through said middle sole so as to have an end positioned at a bottom of said insole.

4. The shoe assembly of claim 1, said electric wire having a linear-shaped end.

5. The shoe assembly of claim 1, said electric connecting portion being a jack.

* * * * *